United States Patent [19]
DiMarco

[11] Patent Number: 5,403,321
[45] Date of Patent: Apr. 4, 1995

[54] RADIOLUCENT DRILL GUIDE

[75] Inventor: Donna M. DiMarco, Memphis, Tenn.

[73] Assignee: Smith & Nephew Richards Inc., Memphis, Tenn.

[21] Appl. No.: 167,740

[22] Filed: Dec. 15, 1993

[51] Int. Cl.⁶ .................................................. A61F 2/32
[52] U.S. Cl. ............................................ 606/96; 606/97
[58] Field of Search ........................... 606/60–68, 606/86, 87, 88, 96, 97, 98, 102, 104

[56] References Cited

U.S. PATENT DOCUMENTS

| | | | |
|---|---|---|---|
| 4,541,424 | 9/1985 | Grosse | 606/97 |
| 4,570,624 | 2/1986 | Wu | 128/92 |
| 4,805,607 | 2/1989 | Engelhardt et al. | 128/92 |
| 4,827,917 | 5/1989 | Brumfield | 128/42 |
| 4,850,344 | 7/1989 | Olerud | 606/97 |
| 4,881,535 | 11/1989 | Sohngen | 606/98 |
| 4,911,153 | 3/1990 | Border | 606/98 |
| 4,978,351 | 12/1990 | Rozas | 606/98 |
| 5,030,222 | 7/1991 | Calandruccio | 606/97 |
| 5,047,034 | 9/1991 | Sohngen | 606/87 |
| 5,084,051 | 1/1992 | Tormala | 606/77 |
| 5,178,621 | 1/1993 | Cook | 606/104 |
| 5,192,327 | 3/1993 | Brantigum | 606/60 |
| 5,207,682 | 5/1993 | Cripe | 606/96 |

FOREIGN PATENT DOCUMENTS

WO93/11713  6/1993  WIPO .

*Primary Examiner*—Michael A. Brown
*Attorney, Agent, or Firm*—Pravel, Hewitt, Kimball & Krieger

[57] ABSTRACT

A radiolucent drill guide for connection to the proximal end portion of an intramedullary nail for aligning a drill with bores of an intramedullary nail when the nail is surgically positioned within a intramedullary canal of a patient includes a handle member of radiolucent material and a guide barrel imbedded within the handle. The handle includes an inner generally cylindrical bore and an outer surface that is bonded to closely surround the radiolucent material of the handle member so that the barrel does not rotate freely relative to the handle. The guide barrel includes flanges for preventing relative movement of the barrel in the direction of the central longitudinal axis of the bore of the barrel. A plurality of openings in the handle are at positions spaced away from the barrel for guiding drills when the barrel is affixed to the intramedullary nail so that the drills align with selected openings of the intramedullary nail.

33 Claims, 4 Drawing Sheets

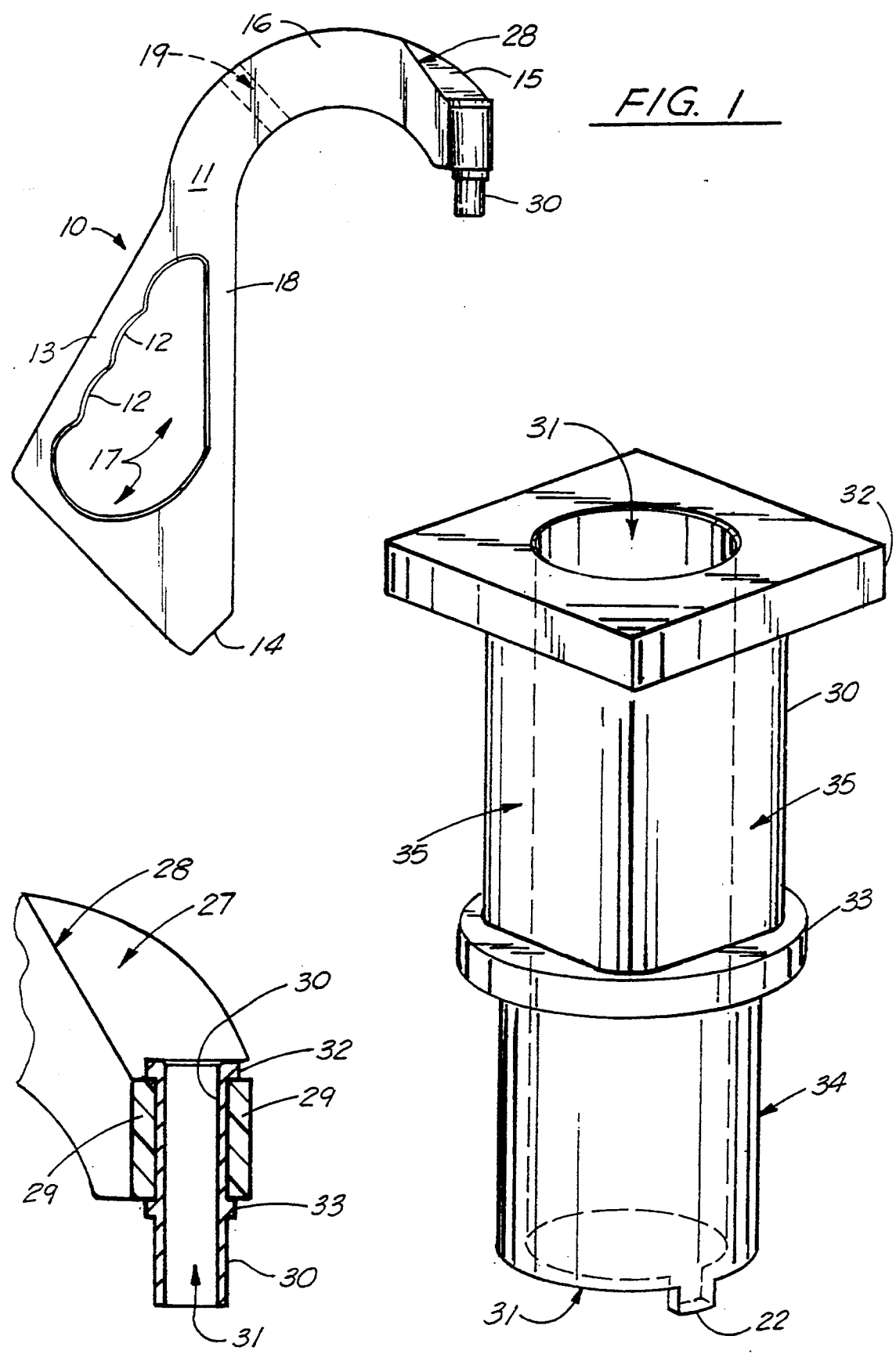

RADIOLUCENT DRILL GUIDE

BACKGROUND OF THE INVENTION

1. Field Of The Invention

The present invention relates to orthopedic surgical instruments and more particularly to an intramedullary rod targeting device in form of a drill guide that is useful in the attachment of an intramedullary nail and associated bone screws to the femur of a patient. Even more particularly, the present invention relates to an improved radiolucent drill guide having a handle portion of radiolucent material and a guide barrel that is imbedded within the handle in such a manner as to resist rotation and/or extrusion from the handle and wherein the barrel does not rotate freely relative to the handle, the handle preferably being molded (eg. injected molded) to the barrel after the barrel is constructed. The apparatus defines a target line which begins at the lateral cortex of a femur, through diagonal openings in the proximal end of an inserted intramedullary femoral rod, through the femoral neck and into the femoral head.

2. General Background

Intramedullary nails are commonly used to repair fractures at various positions on a patient's femur. For example, the intramedullary nail can be placed in a fractured femur with bone screws placed transversely through the femur and through openings in the intramedullary nail. U.S. Pat. No. 4,805,607 issued to Brumfield discloses an intramedullary nail for the repair of long bone fractures. Sometimes, the openings are diagonally placed. For example, U.S. Pat. No. 4,827,917 discloses an intramedullary nail that includes both transverse and diagonally extending openings through which bone screws can be placed as part of an overall repair. U.S. Pat. No. 4,827,917 is hereby incorporated herein for reference.

During an operative procedure, the surgeon places the intramedullary nail within the intramedullary canal of the patient's femur. Thereafter, holes must be drilled in precise locations through the patient's bone tissue and in alignment with the holes that are already a part of the intramedullary nail. A problem with this type of intramedullary nail surgery is the alignment problem. The bone screws must be precisely positioned relative to existing openings in the intramedullary nail. Therefore, targeting devices have been used in the art to insure proper placement of a bone screw relative to the intramedullary nail that has been installed in the patient's intramedullary canal.

A universal guide for inserting parallel pins is disclosed in the Kent Wu patent 4,570,624. The apparatus includes an elongated bar and a plurality of blocks slidable along the bar and adapted to be adjustable locked in position on the bar. Each block supports a transverse opening, the openings in the blocks being parallel to one another. In one form a removable sleeve is provided and has a complimentary external configuration corresponding to the internal configuration of the opening of each block. Each sleeve has an opening therethrough such that when the sleeves are positioned in the openings in the blocks, the openings of the sleeves are parallel to one another. Each sleeve has a serrated end for engagement with a bone of a portion of the body for holding the sleeve in position during drilling of an opening and insertion of a surgical pin.

An intramedullary rod targeting device for drilling of distal fastener screw passages in the femur of a patient during the installation of an intramedullary rod is disclosed in U.S. Pat. No. 4,881,535 issued to Gary Sohngen.

The Robert Border patent 4,911,153 entitled "Orthopedic Surgical Instrument discloses an instrument that serves as an adjustable guide for drills, reamers, fasteners and other orthopedic devices which lie on a target line which extends from the lateral cortex of the femur, through an opening in the proximal end of an inserted intramedullary nail, through the femoral neck and into the femoral head. The instrument can be secured to align with the inserted nail. A handle of the instrument extends downwardly from the top of the nail along the line which is substantially parallel to the target line.

The Rozas patent 4,978,351 provides a guiding instrument to pierce the bone cortical auxiliary in the location of the holes for intramedullary pins.

An intramedullary rod screw guide for use in orthopedic surgical procedures involving the installation of an intramedullary rod is disclosed in U.S. Pat. No. 5,047,034 issued to Sohngen. The Sohngen patent includes a device for attaching the guide to an external support assembly during installation of an intramedullary rod. A laterally extending spacer plate and intramedullary rod attachment at the proximal end of the spacing plate is provided, and a guide is secured to the spacer plate intermediate the proximal and distal ends thereof. The guide forms a passage which in use is lined with bone screw passage in the intramedullary rod permitting the guided insertion of drill means and bone screw insertion means through the guide passage in alignment with the bone screw passage in the intramedullary rod.

One example of a targeting device is U.S. Pat. No. 5,178,621 entitled "Two-Piece Radio-Transparent Proximal Targeting Device for a Locking Intramedullary Nail", issued to Kevin Cook and Karl Ousley. The Cook, et. al. device discloses a targeting device that includes a radio-transparent handle and a metal snap fit barrel. The radio-transparent handle reduces obstructions in the radio-graphic image to provide a clearer image to the surgeon for proper placement of the locking screws. The metal snap-fit barrel is retained in the handle by an interference fit between the handle and biased keys carried by the barrel. After use, the barrel may be easily disassembled for cleaning by striking a removal tool against the keys to drive the barrel from the handle.

An adjustable drill guide for use with an orthopedic implant having sleeves which are adjustable to accommodate misalignment of the sleeve relative to the bores within a prosthetic implant is the subject of U.S. Pat. No. 5,207,682 issued to Philip Cripe. Each sleeve is press-fitted within a retaining ring. The retaining rings are carried within a longitudinal slot of the extending leg of the guide. The rings may be clamped against movement after adjustment of the sleeves.

A published PCT application (PCT application number WO 93/11713) discloses a pilot device for a drill, for making the drilled hole for receiving a screw to be inserted into the neck of a femur, an intramedullary nail already being inserted into the femur. The apparatus includes a pivotable drilling template adjustable for height removably fitted at the proximal end of the intramedullary nail and having at least two drilling holes at a horizontal distance from each other of at least the diameter of the intramedullary nail.

SUMMARY OF THE PRESENT INVENTION

The present invention provides an improved radiolucent drill guide for connection to the proximal end of an intramedullary nail for aligning a drill with the bore of an intramedullary nail when the nail is surgically position within the intramedullary canal of a patient. The apparatus includes a handle member of radiolucent material such as a plastic or polymeric material.

A guide barrel is imbedded within the handle, the handle including an inner generally cylindrical bore and an outer surface that is bonded to and closely surrounded by the radiolucent material of the handle so that the barrel does not rotate freely relative to the handle.

The guide barrel includes flanges for preventing relative movement of the barrel relative to the handle in a direction aligned with the bore of the barrel.

The plurality of openings in the handle are placed in a position spaced away from the barrel for guiding a drill when the barrel is affixed to the intramedullary nail.

The handle can include an arc shaped portion that is spaced away from a gripping portion. The arc shaped portion has a free end that carries the barrel.

The radiolucent material can be of a plastic material such as PEEK, polysulfone, polycarbonate, glass fiber, graphite fiber, polyetherimide, polyethersulfone, polyphenylsulfone and polyphenylsulfide and preferably a material that can be molded such as injection molded.

The method of the present invention provides an improved method of manufacturing a radiolucent drill guide. In the method of the present invention, the barrel is first formed of a metallic material and having a longitudinally extending cylindrical bore. Thereafter, a handle is molded to the barrel with a moldable material. The handle is then allowed to cure. After curing, one or more drill guide openings are milled through the handle at a position spaced away from the barrel.

The moldable material is preferably a plastic, and preferably an injection molded plastic. The barrel has an outer surface with projections that disallow rotation of the barrel relative to the handle. The barrel is preferably bonded sufficiently to the handle to disallow rotation of the barrel relative to the handle.

In one embodiment, the barrel has a generally rectangular cross section that is defined by a plurality of flat surfaces. As part of the method, the moldable material can be PEEK, polysulfone, polycarbonate, polyetherimide, polyethersulfone, polyphenylsulfone, polyphenylsufide, glass fiber, or graphite fiber.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 1 is a side view of the preferred embodiment of the apparatus of the present invention;

FIG. 2 is a partial view of the preferred embodiment of the apparatus of the present invention illustrating the barrel portion thereof;

FIG. 3 is a fragmentary, partial sectional view of the preferred embodiment of the apparatus of the present invention;

DETAILED DESCRIPTION OF THE PREFERRED EMBODIMENT

Figure 4:
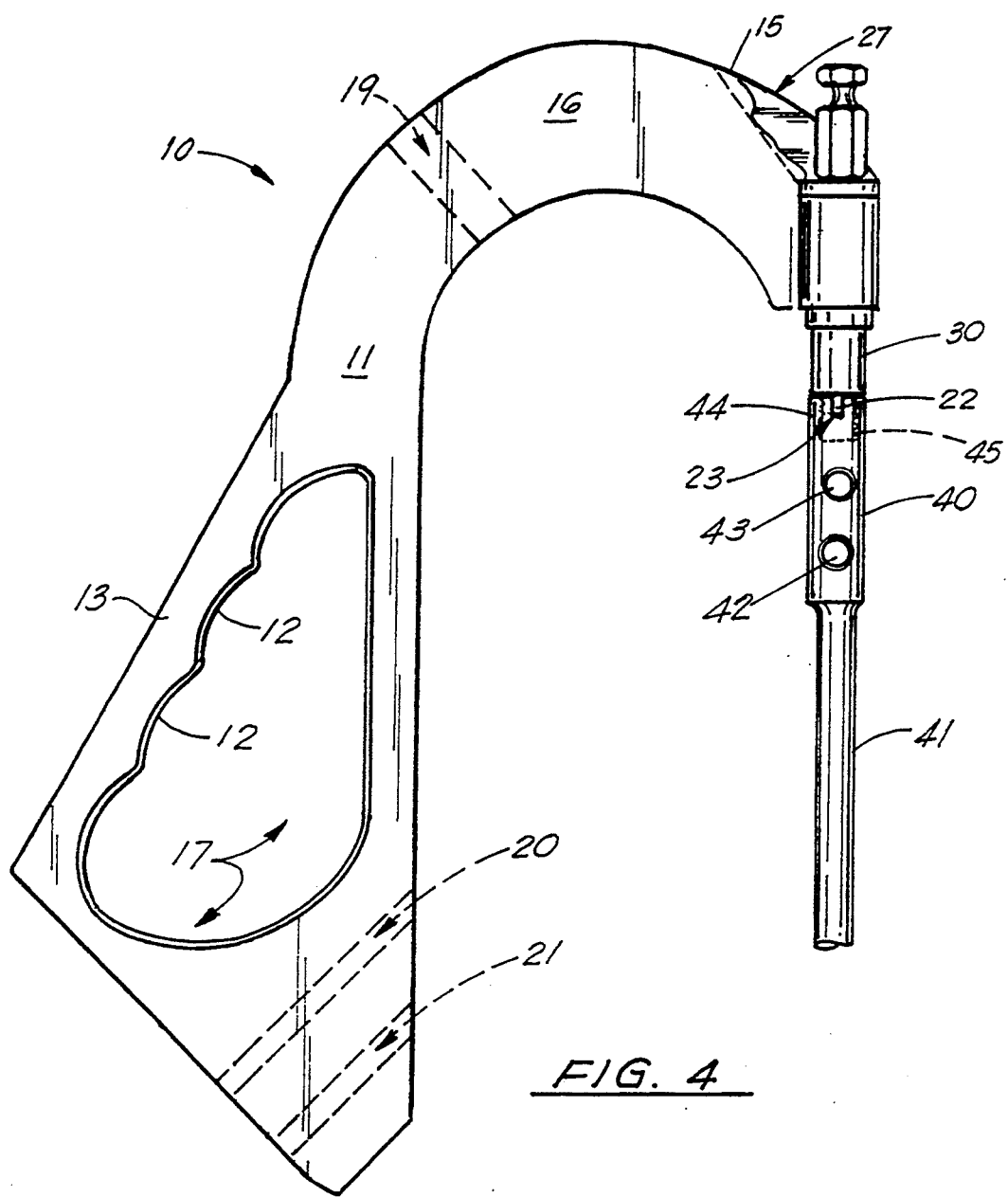
FIG. 4 is a side view of the preferred embodiment of the apparatus of the present invention shown in use with an intramedullary rod.
Figure 5:
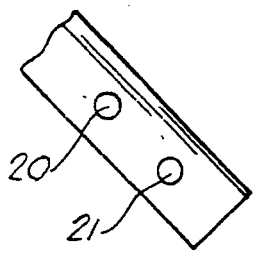
FIG. 5 is a fragmentary view of the preferred embodiment of the apparatus of the present invention illustrating the handle portion thereof.
Figure 6:
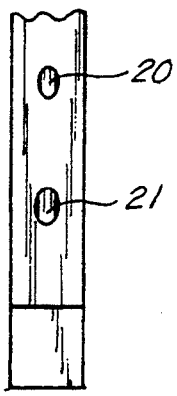
FIG. 6 is another fragmentary view of the preferred embodiment of the apparatus of the present invention illustrating a portion of the handle thereof.
Figure 7:
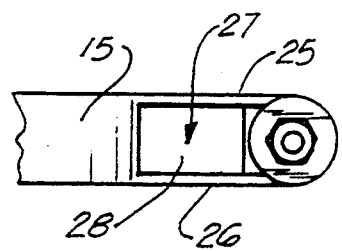
FIG. 7 is a partial fragmentary view of the preferred embodiment of the apparatus of the present invention illustrating a portion of the handle.

FIGS. 1–7 illustrate generally preferred embodiment of the apparatus of the present invention, designating generally by the numeral 10. Radiolucent drill guide 10 includes a handle 11 having a gripping surface 12 for grasping by the hand of a user. The gripping surface 12 is provided adjacent grip 13 which is a narrowed section of material adjacent opening 17.

The handle 11 includes a distal end portion 14 and a proximal end portion 15. The proximal end portion 15 communicates with arc shaped portion 16 extending from grip 13 and strut 18.

A cylindrically shaped bore 19 extends through the arc shaped portion 16 as shown in FIG. 1. A pair of cylindrically shaped bores 20, 21 are provided in the distal end 14 portion of handle 11. The bores 20, 21 are generally parallel and both are perpendicular to the bore 19. Bores 20, 21 define guides for drills that are used to penetrate the patient's bone tissue after the apparatus 10 is mounted upon an intramedullary rod 40 that is imbedded in a patient's intramedullary canal, such as the intramedullary canal of a femur 46. During use, a drill (not shown) is placed through a selected bore 19, 20, or 21. The drill then enters the lateral cortex of the patient's femur, then tracks diagonal openings 42, 43 in the proximal end 44 of intramedullary rod 40. The drill continues through the patient's femoral neck 47 and can extend into the femoral head 48.

Proximal end 15 of handle 11 provides a pair of spaced apart flanges 25, 26 with a recess 27 therebetween. An inclined surface 28 also surrounds recess 27. During use, the recess 27 provides a space that allows a nail puller element 36 to be placed through the bore 31 of barrel 30.

Barrel 30 is mounted in handle 11 at the proximal end portion 15 thereof. Closely surrounding annular portion 29 of plastic material comprises a portion of handle 11 which closely surrounds barrel 30. In the preferred embodiment, the handle 11 is of a plastic material and can be molded such as injection molded to barrel 30 after the barrel 30 has been constructed of metal for example.

In FIG. 2, barrel 30 is shown as including a pair of spaced apart flange portions 32 and 33. The flange 32 is a square flange while the flange 33 can be a round flange. Barrel 30 includes an outer generally cylindrically surface 34 and can include a plurality of flat surfaces (for example four flat sections 35). The flat surfaces 35 in combination with the closely surrounding plastic material 29 of handle 11 insures that the barrel 30 will not rotate relative to barrel 11. The flange portions 32 and 33 on the barrel 30 prevent relative movement of the barrel 30 relative to the handle 11 in a direction aligned with the bore of the barrel 30.

Figure 9:
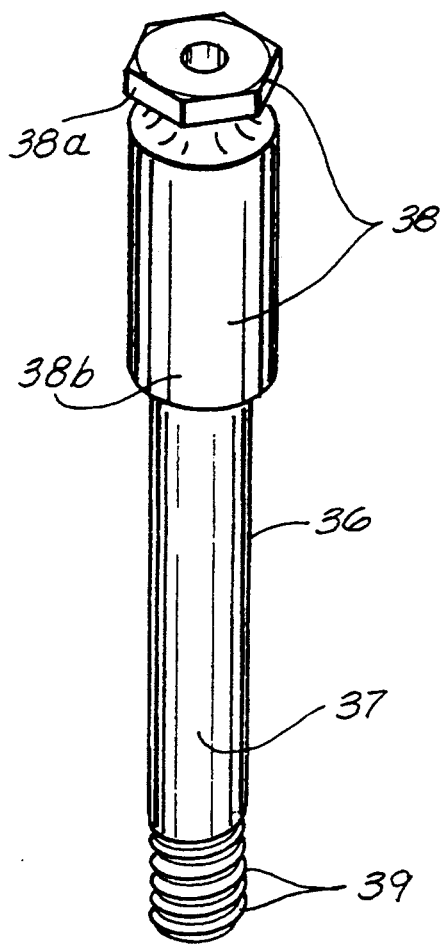
FIG. 9 is a partial perspective view of the preferred embodiment of the apparatus of the present invention illustrating the nail puller element portion thereof.
Figure 10:
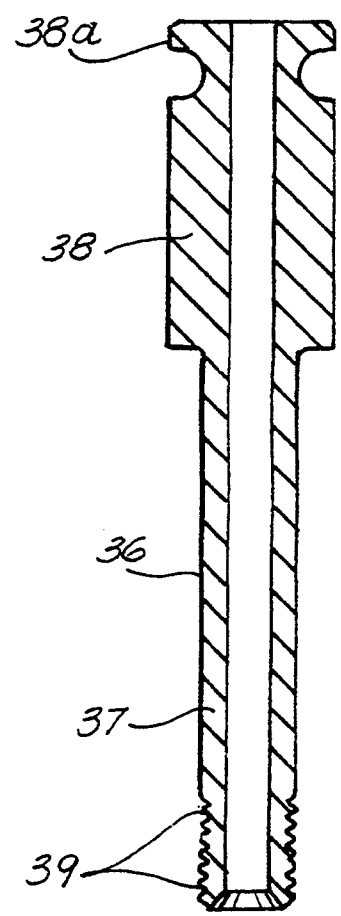
FIG. 10 is a sectional view of the nail puller element of FIG. 9.

The barrel 30 provides a longitudinally extending central cylindrically shaped bore 31 that can be occupied during use with nail puller element 36. Nail puller element 36 (FIGS. 9–11) comprises a shank portion 37 that is generally cylindrically shaped having an outer surface that corresponds in shape to, but is slightly smaller in diameter than the bore 31 of barrel 30. Shank portion 37 is connected to an enlarged hexagonally shaped head 38 and provides a portion having external threads 39. The external threads 39 of nail puller element 36 communicate with corresponding internal threads 45 on the inside bore 41 of intramedullary rod 40. The proximal head 38 of the nail puller element 36 can have a hexagonal shaped portion 38a, or a cylindrically shaped portion 38b.

Intramedullary rod 40 is a commercially available rod that includes a longitudinally extending bore 41 extending throughout its length, terminating a closed end portion of the intramedullary rod 40 at its lower distal end, generally opposite proximal head 44. Internal threads 45 allow the attachment of nail puller 36 thereto and wherein the central longitudinal axis of the nail puller element 36 corresponds with the central longitudinal axis of bore 31 and with the central longitudinal axis of bore 41 at proximal end 44 of rod 40. The moldable radiolucent material can be PEEK, polysuflone, polycarbonate, polyetherimide, polyethersulfone, polyphenylsulfone, polyphenylsufide, glass fiber, or graphite fiber.

Figure 8:
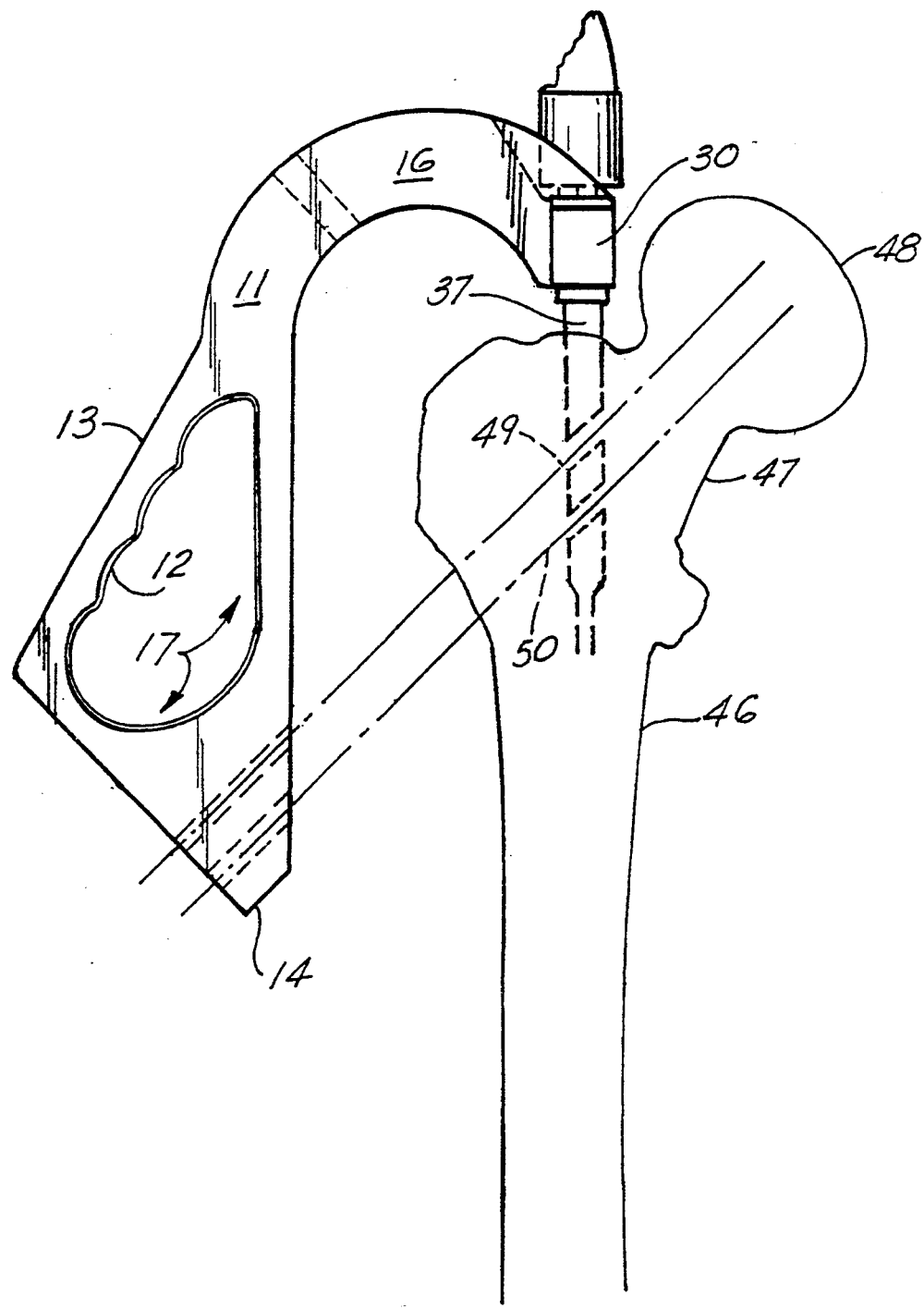
FIG. 8 is a side schematic view of the preferred embodiment of the apparatus of the present invention shown upon a patient's femur and during a drilling of openings thereunto.

During operation, the intramedullary rod 40 is first placed in a patient's femur 46. The femur 46 includes a femoral neck 47 and a femoral head 48. In order to repair a fracture in the upper, proximal region of femur 46, one or more drill members are sequentially placed in the bores 20, 21 of drill guide handle 11. In FIG. 8, the numerals 49, 50 designate the paths tracked by drills that are inserted into bores 20, 21. The drills track the paths 49, 50 and extend a distance into the femoral neck 47 or femoral head 48 as selected by the surgeon depending upon the fracture to be repaired.

Before drilling, the nail puller element 36 is threaded to the intramedullary rod 40 as shown in FIG. 4. This produces an alignment of nail puller element 36 and also of the central longitudinal bore 31 of barrel 30 in a desired position relative to intramedullary rod 40 and femur 46. A pair of indexing tabs 22 are placed 180° apart on barrel 30. A pair of correspondingly shaped recesses 23 are placed 180° apart on the top, proximal end of rod 40. The tabs 22 interlock with the recesses 23 to properly orient diagonal openings 42, 43 with bores 20, 21 and axes 49, 50. The central axis of a drill inserted into bore 20 or 21 tracks axis 49 or 50 and also tracks the central axis of a diagonal opening 42, 43.

The handle bores 20, 21 are thus aligned with openings 42, 43 of rod 40. Drills placed in bores 20, 21 perfectly line-up with diagonal openings 42, 43 of intramedullary rod 40. In FIG. 4, the openings 42, 43 are shown in a misaligned position to show the openings 42, 43 and their location on head 44 of intramedullary rod 40.

The following table lists the part numbers and part descriptions as used herein and in the drawings attached hereto.

| PARTS LIST | |
|---|---|
| Part Number | Description |
| 10 | Radiolucent drill guide |
| 11 | handle |
| 12 | gripping surface |
| 13 | grip |
| 14 | distal end |
| 15 | proximal end |
| 16 | arc shaped portion |
| 17 | opening |
| 18 | strut |
| 19 | cylindrical bore |
| 20 | bore |
| 21 | bore |
| 22 | indexing tab |
| 23 | recess |
| 25 | flange |
| 26 | flange |
| 27 | recess |
| 28 | inclined surface |
| 29 | surrounding annular portion |
| 30 | barrel |
| 31 | cylindrical bore |
| 32 | square flange |
| 33 | round flange |
| 34 | cylindrical outer surface |
| 35 | flat surface |
| 36 | nail puller element |
| 37 | shank portion |
| 38 | enlarged head |
| 38a | hexagonal section |
| 38b | cylindrical section |
| 39 | external threads |
| 40 | intramedullary rod |
| 41 | smaller diameter bore |
| 42 | diagonal opening |
| 43 | diagonal opening |
| 44 | proximal head |
| 45 | internal threads |
| 46 | femur |
| 47 | femoral neck |
| 48 | femoral head |
| 49 | drill path |
| 50 | drill path |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A radiolucent drill guide for connection to the proximal end of an intramedullary nail for aligning a drill with bores of an intramedullary nail when the nail is surgically positioned within an intramedullary canal of a patient, comprising:
   a) a handle member of radiolucent material;
   b) a guide barrel imbedded within the handle, the handle including an inner generally cylindrical bore and an outer surface that is rigidly attached to the radiolucent material of the handle member so that the barrel does not rotate freely relative to the handle;

c) the guide barrel having an outer surface with flange means thereon for preventing movement of the barrel relative to the handle in a direction along the bore of the barrel; and d) a plurality of openings in the handle at a position spaced away from the barrel for guiding a drill relative to the nail when the barrel is affixed to the intramedullary nail.

2. The drill guide of claim 1 wherein the handle includes an arc shaped portion.

3. The drill guide of claim 1 wherein the radiolucent material is plastic.

4. The drill guide of claim 1 wherein the radiolucent material is PEEK.

5. The drill guide of claim 1 wherein the radiolucent material is polysulfone.

6. The drill guide of claim 1 where in the radiolucent material is polycarbonate.

7. The drill guide of claim 1 wherein the radiolucent material is glass fiber.

8. The drill guide of claim 1 wherein the radiolucent material is polyetherimide.

9. The drill guide of claim 1 wherein the radiolucent material is polyethersylfone.

10. The drill guide of claim 1 wherein the radiolucent material is polyphenylsulfone.

11. The drill guide of claim 1 wherein the radiolucent material is polyphenylsulfide.

12. The drill guide of claim 1 wherein the radiolucent material is graphite fiber.

13. The drill guide of claim 1 wherein the radiolucent material is material that can be molded.

14. The drill guide of claim 1 wherein the radiolucent material is material that can be injection molded.

15. The drill guide of claim 1 wherein the barrel includes projections on the outer surface thereof that prevents rotation of the barrel relative to the handle.

16. The drill guide of claim 1 wherein the radiolucent material is injection molded plastic that is injection molded to the barrel.

17. The drill guide of claim 1 wherein the barrel has a plurality of flat surfaces on its outer surface.

18. A method of manufacturing a radiolucent drill guide comprising of steps of:

a) forming a barrel of metallic material with a cylindrical bore and an outer surface radially spaced from bore;

b) molding a handle to the barrel outer surface with a moldable material;

c) allowing the handle to cure;

d) machining one or more drill guide openings through the handle at a position spaced away from the barrel; and e) further comprising the step of maintaining connection of the barrel to the handle after curing is completed in step "c" so that the barrel does not rotate relative to the handle.

19. The method of claim 18 wherein in step "b" the material is plastic.

20. The method of claim 18 wherein in step "a" the barrel has an outer surface with projections that disallow rotation of the barrel relative to the handle.

21. The method of claim 18 wherein in step "a" the barrel bonded to the sufficiently to disallow rotation of the barrel relative to the handle.

22. The method of claim 18 wherein the barrel has a central, cylindrically shaped bore.

23. The method of claim 18 wherein the barrel has a generally rectangular cross section.

24. The method of claim 18 wherein step "b" the plastic material is injection molded plastic.

25. The method of claim 18 wherein the handle is of a PEEK material.

26. The method of claim 18 wherein the handle is of a polysulfone material.

27. The method of claim 18 wherein the handle is of a polycarbonate material.

28. The method of claim 18 wherein the handle is of a glass fiber material.

29. The method of claim 18 wherein the handle is of a graphite fiber material.

30. The method of claim 18 wherein the handle is of a polyetherimide material.

31. The method of claim 18 wherein the handle is of a polyethersylfone material.

32. The method of claim 18 wherein the handle is of a polyphenylsulfone material.

33. The method of claim 18 wherein the handle is of a polyphenylsulfide material.

* * * * *